United States Patent
Watanabe et al.

(10) Patent No.: US 10,281,436 B2
(45) Date of Patent: May 7, 2019

(54) ACOUSTIC WAVE ACQUISITION APPARATUS AND METHOD FOR CONTROLLING THE SAME

(71) Applicant: CANON KABUSHIKI KAISHA, Tokyo (JP)

(72) Inventors: Tadaki Watanabe, Nagoya (JP); Daisuke Nagao, Kawaguchi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/812,752

(22) Filed: Nov. 14, 2017

(65) Prior Publication Data

US 2018/0136171 A1 May 17, 2018

(30) Foreign Application Priority Data

Nov. 17, 2016 (JP) .................. 2016-224384

(51) Int. Cl.
| | | |
|---|---|---|
| *G01N 29/07* | (2006.01) | |
| *G01N 29/24* | (2006.01) | |
| *G01N 29/06* | (2006.01) | |
| *G01N 29/11* | (2006.01) | |
| *G01N 29/265* | (2006.01) | |
| *G01N 29/09* | (2006.01) | |

(52) U.S. Cl.
CPC ..... *G01N 29/2406* (2013.01); *G01N 29/0681* (2013.01); *G01N 29/07* (2013.01); *G01N 29/11* (2013.01); *G01N 29/2437* (2013.01); *G01N 29/265* (2013.01); *G01N 29/09* (2013.01); *G01N 29/2487* (2013.01)

(58) Field of Classification Search
CPC ............. G01N 29/2406; G01N 29/265; G01N 29/2437; G01N 29/0681; G01N 29/07; G01N 29/11; G01N 29/09; G01N 29/2487
See application file for complete search history.

(56) References Cited

U.S. PATENT DOCUMENTS

2015/0327771 A1* 11/2015 Baba .................... A61B 5/0095
600/407

FOREIGN PATENT DOCUMENTS

JP  2011229620 A  11/2011

* cited by examiner

*Primary Examiner* — Kyoung Lee
(74) *Attorney, Agent, or Firm* — Canon U.S.A., Inc. IP Division

(57) ABSTRACT

An acoustic wave acquisition apparatus moves a probe so that, in a case where a distance between a probe positioned at a first point and a second point corresponding to a target position is below a predetermined threshold value, a ratio of a length of a trajectory to a distance between the first point and the second point is larger than in a case where the distance between the probe and the second point exceeds the predetermined threshold value.

13 Claims, 10 Drawing Sheets

FIG.7
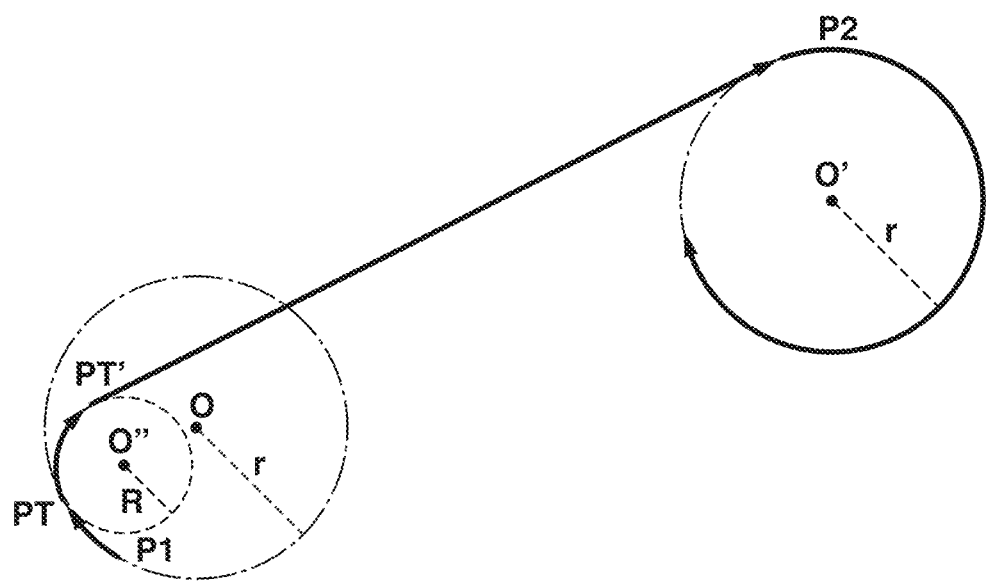
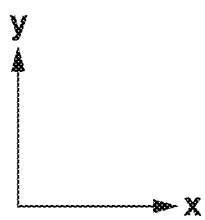

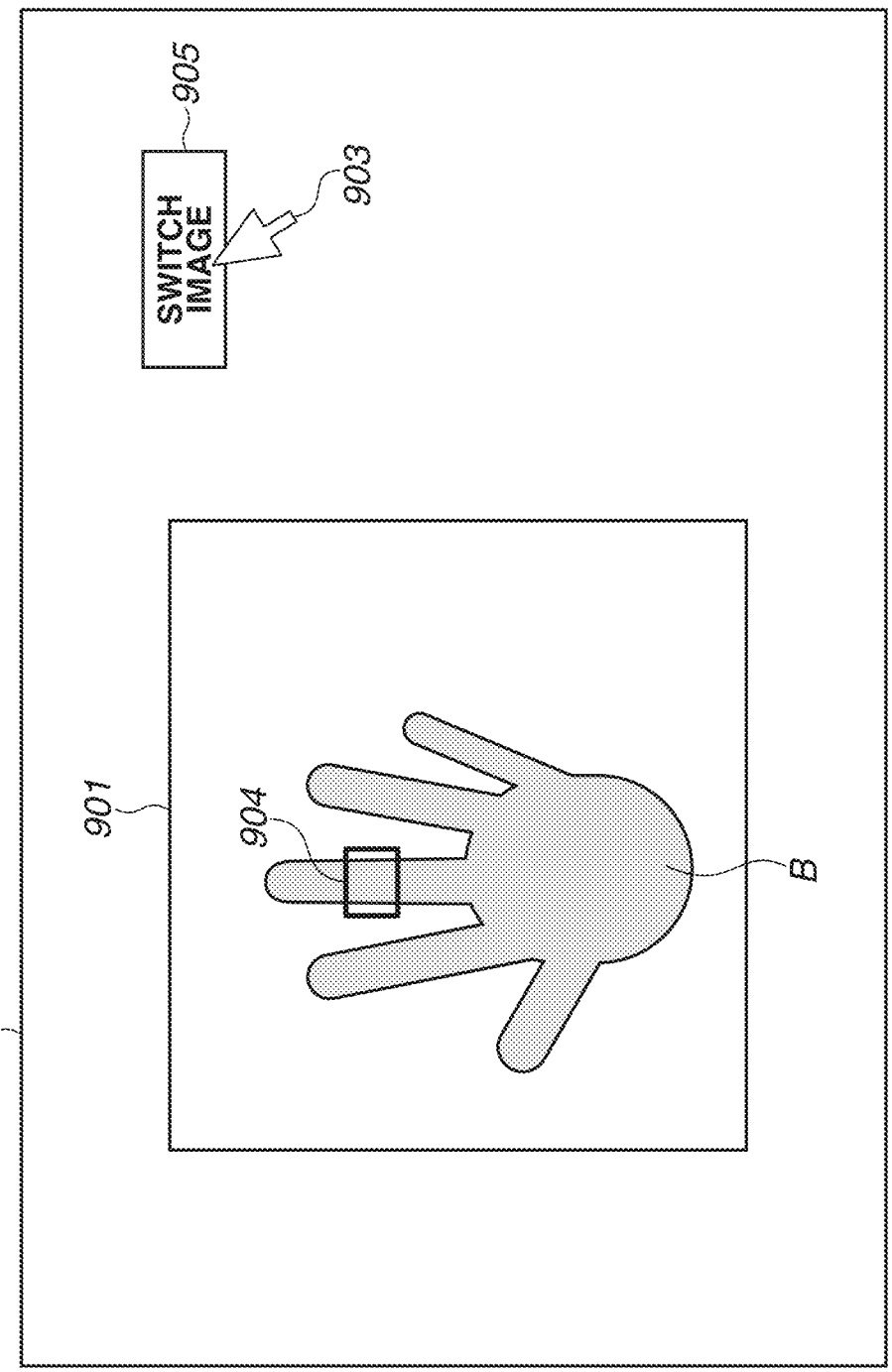

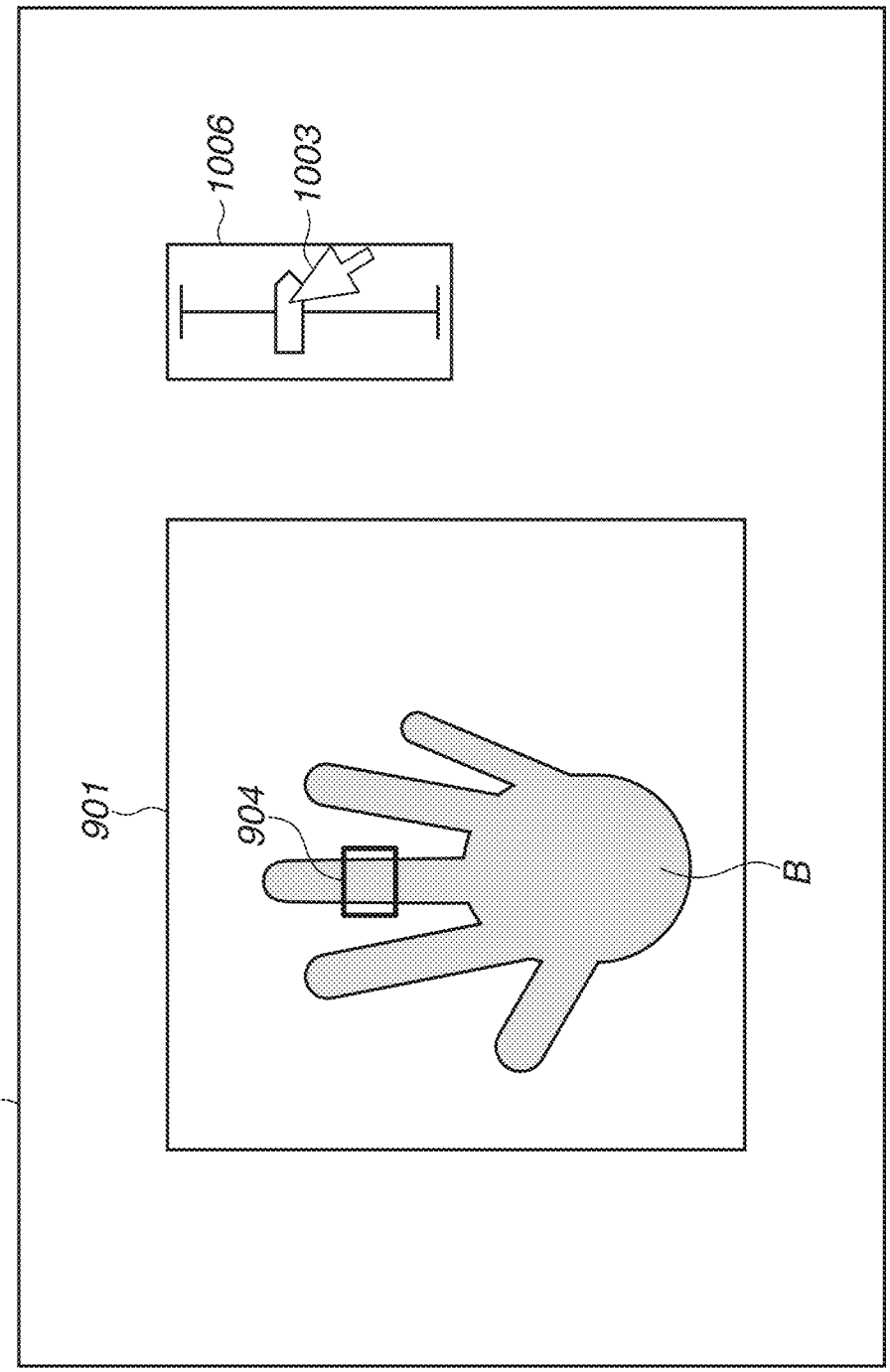

ACOUSTIC WAVE ACQUISITION APPARATUS AND METHOD FOR CONTROLLING THE SAME

BACKGROUND OF THE INVENTION

Field of the Invention

The present invention relates to an acoustic wave acquisition apparatus of a scanning type and a method for controlling the acoustic wave acquisition apparatus.

Description of the Related Art

A scanning-type acoustic wave acquisition apparatus has been known. For example, Japanese Patent Application Laid-Open No. 2011-229620 discusses an acoustic wave measurement apparatus capable of moving an irradiation unit and an acoustic wave probe to a position corresponding to a designated measurement position when an operator of the acoustic wave measurement apparatus designates a measurement position from a subject image captured by a camera.

SUMMARY OF THE INVENTION

In an apparatus described in Japanese Patent Application Laid-Open No. 2011-229620, when a measurement position is designated by an operator while a probe is moving, the moving direction of the probe may be quickly changed so that the probe may be moved to the measurement position. However, quickly changing the moving direction of the probe may cause an unstable orientation of the probe due to the quick change of the moving direction of the probe. It is not desirable that signals acquired while the orientation of the probe is unstable are used for measurement. Particularly in the case where a relatively close position is designated as a measurement position, a quick change of the moving direction of the probe is not preferable since it is desirable that measurement can be continuously performed.

According to an aspect of the present invention, an acoustic wave acquisition apparatus includes a probe configured to receive an acoustic wave propagated from a subject, a moving unit configured to move the probe relative to the subject, a target position designation unit configured to designate a target position to which the probe is to be moved, and a movement control unit configured to control the moving unit to move the probe along a trajectory. The movement control unit determines the trajectory so that, in a case where a distance between the probe positioned at a first point and a second point corresponding to the target position is below a predetermined threshold value, a ratio of a length of the trajectory to a distance between the first point and the second point is larger than in a case where the distance between the probe and the second point exceeds the threshold value.

According to another aspect of the present invention, a method for controlling an acoustic wave acquisition apparatus including a probe configured to receive an acoustic wave propagated from a subject, and a moving unit configured to move the probe relative to the subject, includes displaying an image of the subject, receiving an input of a target position in the image, and moving the probe according to the input of the target position. In a case where a distance between the probe and a position corresponding to the target position is below a threshold value, a ratio of a length of a trajectory along which the probe is moved to the distance is larger than in a case where the distance exceeds the threshold value.

According to yet another aspect of the present invention, an acoustic wave acquisition apparatus includes a probe configured to receive an acoustic wave propagated from a subject, a moving unit configured to move the probe relative to the subject, a movement control unit configured to control a movement of the probe by the moving unit, a display control unit configured to cause a display unit to display a first image of the subject captured at a first angle of view and a second image of the subject captured at a second angle of view narrower than the first angle of view, and a position designation unit configured to designate a position in the first or the second image. In a case where a position in the second image is designated by the position designation unit, the movement control unit moves the probe to a position corresponding to the designated position along a more curved trajectory than in a case where a position in the first image is designated.

Further features of the present invention will become apparent from the following description of exemplary embodiments with reference to the attached drawings.

BRIEF DESCRIPTION OF THE DRAWINGS

FIG. 7 illustrates yet another motion of the probe according to the first exemplary embodiment of the present invention.

FIG. 9 illustrates an example of display of a display unit according to a second exemplary embodiment of the present invention.

FIG. 10 illustrates an example of display of a display unit according to a third exemplary embodiment of the present invention.

DESCRIPTION OF THE EMBODIMENTS

Various exemplary embodiments of the present invention will be described below with reference to the accompanying drawings.

Figure 1:
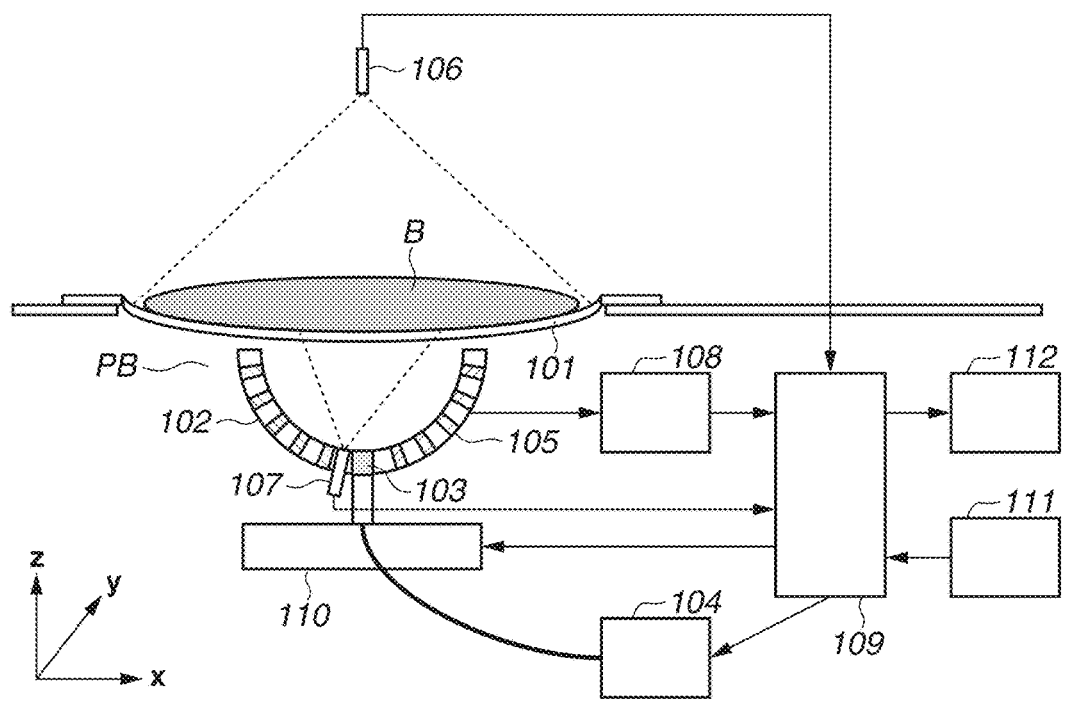
FIG. 1 illustrates an example of a configuration of an acoustic wave acquisition apparatus according to a first exemplary embodiment of the present invention.

FIG. 1 illustrates an example of a configuration of an acoustic wave acquisition apparatus according to a first exemplary embodiment. The acoustic wave acquisition apparatus according to the present exemplary embodiment is a subject information acquisition apparatus for irradiating a subject with light and acquiring subject information based on a photoacoustic wave generated in the subject.

The acoustic wave acquisition apparatus according to the present exemplary embodiment includes a holding member 100, a table 101, a supporting unit 102, a light irradiation unit 103, a light source 104, transducers 105, a first imaging unit 106, a second imaging unit 107, an electrical signal processing unit 108, a control unit 109, a moving unit 110, a measurement position designation unit 111, and a display unit 112. According to the present exemplary embodiment, a subject B is held by the holding member 100. A probe according to the present exemplary embodiment includes a plurality of transducers 105 as acoustic wave detection elements, the light irradiation unit 103, and the supporting unit 102.

The holding member 100 fixes the subject B so that the subject B does not move during image capturing. The holding member 100 is a cup-shaped member made of synthetic resin. It is not necessary that the entire subject B is held by the holding member 100 as long as a region of the subject B to be measured is held. As long as the subject B can be fixed, the holding member 100 may be made of a thin film such as latex rubber. In the following description, unless otherwise specified, the region of the subject B is also referred to as the subject B. To prevent the attenuation of pulsed light serving as measurement light to be applied to the subject B, it is desirable that the holding member 100 is made of a material having high light transmissivity. It is also desirable that the holding member 100 is made of such a material that makes it possible to capture an image of the subject region by using the second imaging unit 107. To reduce the acoustic wave reflection at the interface with the subject B, it is further desirable that the holding member 100 is made of a material having an acoustic impedance close to the acoustic impedance of the subject B. Referring to FIG. 1, the holding member 100 is configured to be supported by the table 101 provided with an opening into which the holding member 100 can be inserted.

The supporting unit 102 has a hemispherical housing on which the plurality of transducers 105 and the second imaging unit 107 are disposed. According to the present exemplary embodiment, the plurality of transducers 105 functions as a probe. As illustrated in FIG. 1, the supporting unit 102 is bowl-shaped to hold an acoustic matching material therein so as to efficiently transmit acoustic waves to the transducers 105. However, the shape of the supporting unit 102 is not limited to a hemisphere as long as the supporting unit 102 has a concave portion for storing a liquid.

The light irradiation unit 103 is disposed at the bottom of the supporting unit 102, and the plurality of transducers 105 is disposed in a spiral form centering on the axis of the bowl-shaped supporting unit 102.

The light irradiation unit 103 functions as an irradiation unit for irradiating the subject B with measurement light. The measurement light is typically pulsed light. The light irradiation unit 103 radiates the measurement light supplied from the light source 104 in the direction from the bottom of the supporting unit 102 toward the center of the hemisphere. In the configuration illustrated in FIG. 1, the measurement light is emitted in the positive direction of the z axis.

Each of the transducers 105 is an element for converting an acoustic wave propagated from the subject B into an electrical signal, more specifically, a piezo-electrical element and an ultrasonic transducer such as a Capacitive Micromachined Ultrasound Transducer (CMUT). Generally, a transducer has directivity to the incidence angle of an acoustic wave, and for this reason, it is desirable that the transducers 105 are fixed to have the maximum sensitivity in a direction toward the center of the hemisphere formed by the supporting unit 102. Although directivity axes of the plurality of transducers 105 do not need to intersect with each other at one point, it is desirable that the directivity axes concentrate near the center of the hemisphere.

The first imaging unit 106 is disposed at the position facing the supporting unit 102 across the subject B, and is configured to capture an image of the subject B in the direction toward the negative direction of the z axis. The first imaging unit 106 may be supported by the table 101 or may be disposed, for example, on the ceiling of a room in which the acoustic wave acquisition apparatus is installed.

The second imaging unit 107 is disposed on the supporting unit 102 and is supported toward the center of the hemisphere.

The first and the second imaging units 106 and 107 can each capture a still image and a moving image, and image sensors such as complementary metal oxide semiconductor (CMOS) sensors and charge coupled device (CCD) sensors can be used. A filter (near-infrared filter, etc.) for reducing incident measurement light may be disposed in the first and the second imaging units 106 and 107.

The electrical signal processing unit 108 is an apparatus for applying signal processing to the electrical signals output from the transducers 105 and transmitting the signals to the control unit 109. The electrical signal processing unit 108 may convert the electrical signals from the transducers 105 into digital signals, amplify the signals, and control the delay amount. It is desirable that the electrical signal processing unit 108 is connected to a light detection sensor attached to the light irradiation unit 103, for example, and acquire a signal in synchronization with the laser light emission. The electrical signal processing unit 108 includes an analog amplifier, an analog-to-digital (A/D) converter, and a noise reduction circuit.

The moving unit 110 is an apparatus which is fixed to the supporting unit 102 by a fixing unit (not illustrated) and moves the supporting unit 102 within the xy plane. A motor-driven XY stage on which a stepping motor is mounted is an example of the moving unit 110. The moving unit 110 moves the supporting unit 102 to change the positions of the light irradiation unit 103 and the transducers 105 (fixed to the supporting unit 102) relative to the subject B. The moving unit 110 may be configured to move the supporting unit 102 also in the z-axis direction.

The measurement position designation unit 111 also serving as an input unit includes at least one of a touch panel, a mouse, and a keyboard, and allows the operator to designate a position at which measurement is to be performed with an optical acoustic wave. More specifically, in the image of the subject B displayed on the display unit 112, the operator taps or clicks a desired measurement position or inputs coordinates information on the image to designate a measurement position. Not only a touch panel but also a liquid crystal display (LCD) not having touch functions or cathode ray tube (CRT) display can be used as the display unit 112. In addition to measurement using an optical acoustic wave, the acoustic wave acquisition apparatus may transmit ultrasonic waves from the transducers 105 toward the subject B, and acquire subject information by using the reflected wave. The measurement position designation unit 111 also functions as a target position designation unit.

The control unit 109 is connected with the light source 104, the electrical signal processing unit 108, the measurement position designation unit 111, the moving unit 110, and the first and the second imaging units 106 and 107 via universal serial bus (USB) interfaces. The control unit 109 is an apparatus for controlling each unit, and has the functions of a movement control unit and a display control unit. The control unit 109 according to the present exemplary embodiment also has a function of a reconfiguration unit configured to reconfigure characteristic information indicating the characteristics inside the subject B by using the signal received from the electrical signal processing unit 108. The characteristic information includes the distribution of the initial sound pressure of a photoacoustic wave generated in the subject B, the light energy absorption density distribution derived from the initial sound pressure, the absorption coefficient distribution, and density distributions of materials of tissues. The control unit 109 controls input/output units to display the reconfigured characteristic information. For example, the control unit 109 can be implemented by a personal computer (PC). An application specific integrated circuit (ASIC) or a field programmable gate array (FPGA) can also be used as another implementation means.

Operations of the acoustic wave acquisition apparatus according to the present exemplary embodiment will be described below.

Figure 2:
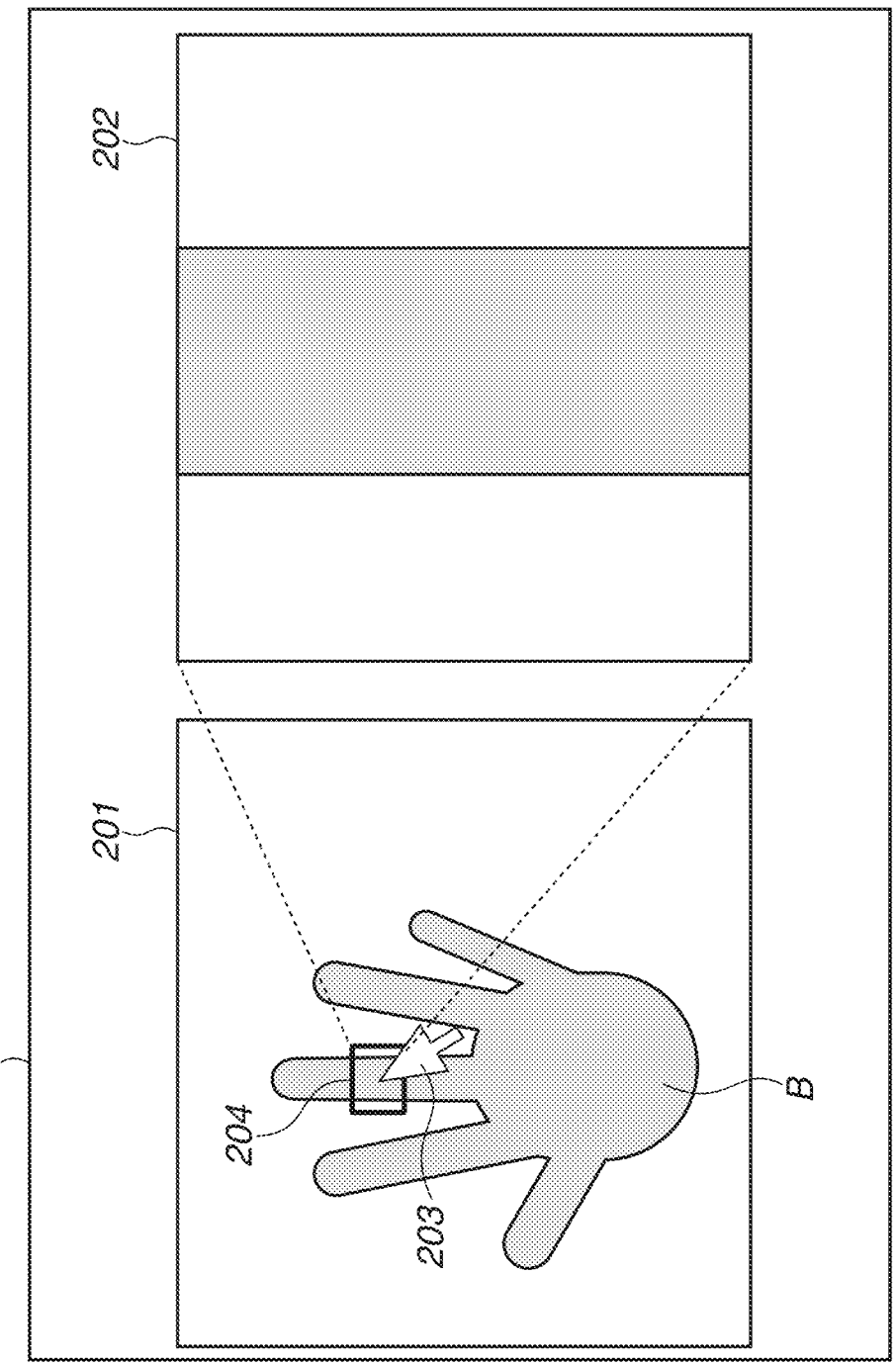
FIG. 2 illustrates an example of display of a display unit according to the first exemplary embodiment.

FIG. 2 illustrates an example of display of the display unit 112. According to the present exemplary embodiment, a first image 201 of the subject B captured by using the first imaging unit 106 and a second image 202 captured by using the second imaging unit 107 are displayed side by side on a screen 200. The angle of view of the second imaging unit 107 is narrower than the angle of view of the first imaging unit 106. To make it easier for the operator to recognize an area displayed on the image 202, the area is indicated by a frame 204 displayed on the image 201. The operator designates a position at which photoacoustic measurement is to be performed by using the measurement position designation unit 111. Referring to FIG. 2, when the operator selects a measurement position by using the cursor 203, the frame 204 is displayed centering on the designated position. Accordingly, the control unit 109 instructs the moving unit 110 to move the supporting unit 102. Although, in this case, the operator designates a position in the image 201 captured by using the first imaging unit 106, the operator can also designate a position in the image 202 captured by using the second imaging unit 107. Even when the operator designates a position in the second image 202, the supporting unit 102 is moved so that the designated position comes to the center. A photoacoustic image based on an acquired acoustic wave may be further displayed on the screen 200.

The first image 201 has a wider angle of view than the second image 202. Therefore, the first image 201 is useful when the supporting unit 102 is moved over a comparatively long distance, and the second image 202 is useful when the supporting unit 102 is moved over a comparatively short distance. Therefore, when a measurement position is to be designated in the first image 201, it is desirable to quickly move the supporting unit 102 to the designated position. On the other hand, when a measurement position is to be designated in the second image 202, it is desirable, as the moving distance is short, to give higher priority to the continuity of images in the process of moving the supporting unit 102 to the designated measurement position than to the time period till the supporting unit 102 reaches the measurement position. According to the present exemplary embodiment, the control unit 109 performs control so that, when the operator designates a position in the first image 201 as a measurement position, the trajectory along which the supporting unit 102 is moved to the measurement position is more linear than the trajectory when the operator designates a position in the second image 202 as a measurement position. In other words, according to the acoustic wave acquisition apparatus according to the present exemplary embodiment, in the case where the distance between the position of the supporting unit 102 and a designated measurement position when the operator designates the measurement position is below a predetermined threshold value, the supporting unit 102 is moved along a more curved trajectory than in the case where the distance exceeds the threshold value.

A trajectory along which the supporting unit 102 is to be moved to a designated measurement position will be described below.

Figure 3:
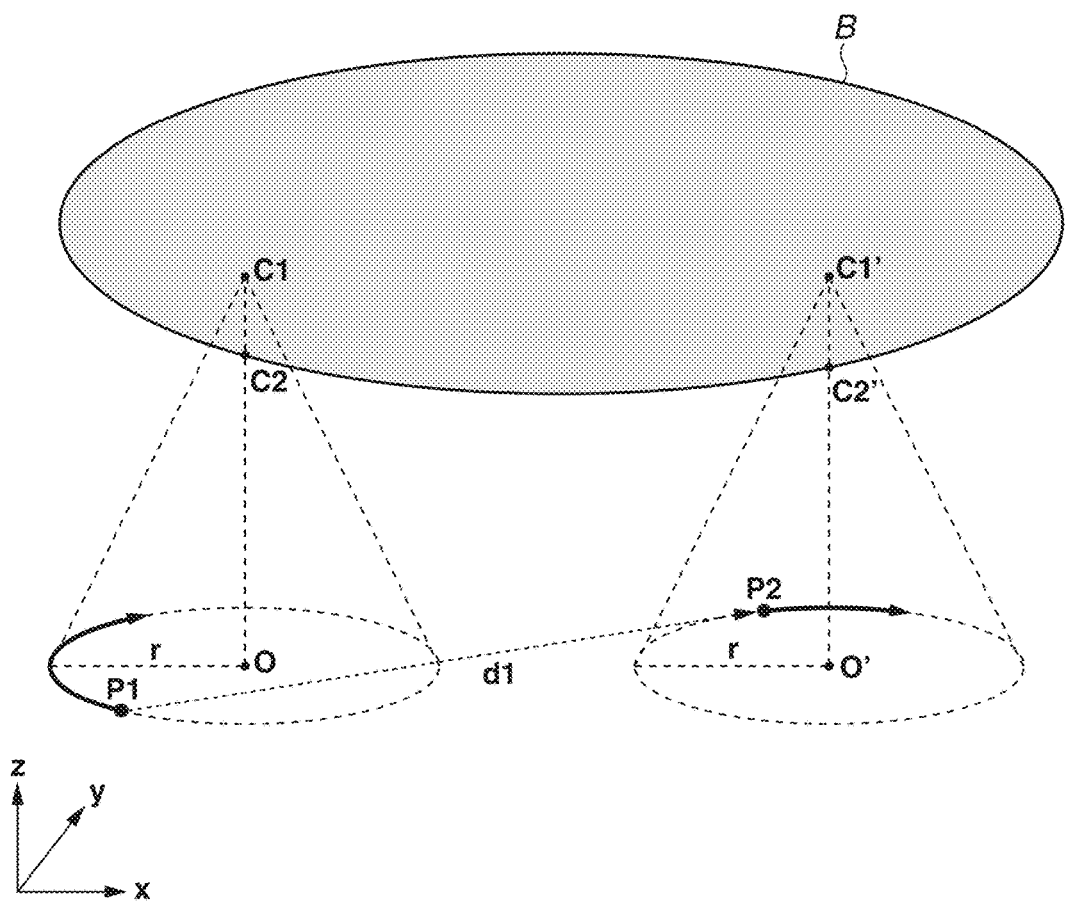
FIG. 3 illustrates a motion of a probe according to the first exemplary embodiment of the present invention.

Referring to FIG. 3, the probe is being moved in the clockwise direction along a circular trajectory with a radius r centering on a point O in the xy plane before designation of a measurement position by the operator is received. While the probe PB is being moved along this circular trajectory, the light irradiation unit 103 repetitively irradiates the subject B with the measurement light, and acoustic waves are repetitively received. Since acoustic waves generated from the region including the point P in the subject B can be acquired from a plurality of directions, the subject information about this region can be obtained with high precision. The subject information obtained based on the acquired acoustic waves can also be displayed on the display unit 112 in real time.

The operator designates a measurement position by using the measurement position designation unit 111. The operator can designate a measurement position in the image of the subject B displayed on the display unit 112. More specifically, the operator can select a measurement position by clicking the position in the image of the subject B with the mouse, inputting the coordinates from the keyboard, or tapping the position if the display unit is provided with a touch panel. In this case, since the image of the subject B is an image captured by an optical camera, the operator will designate a point C2' on the surface of the subject B as a measurement position.

Upon reception of the measurement position designation, the control unit 109 controls the moving unit 110 to move the probe PB to the position corresponding to the designated measurement position. In this case, the probe PB is moved to a point P2 on the circumference which forms the bottom of the cone having as a vertex a point C1' on the normal passing through the point C2'. The point P2 is the target position to which the probe PB is to be moved. Although, in this example, the circular trajectory before a measurement position designation is received and the circular trajectory including the point P2 have the same radius size, the two radius sizes may not necessarily be the same. Suppose that the probe PB is at the point P1 when the control unit 109 instructs the moving unit 110 to move the probe PB to the point P2. In the following description, a circle having a center at the point O is also referred to as a circle O.

Figure 4:
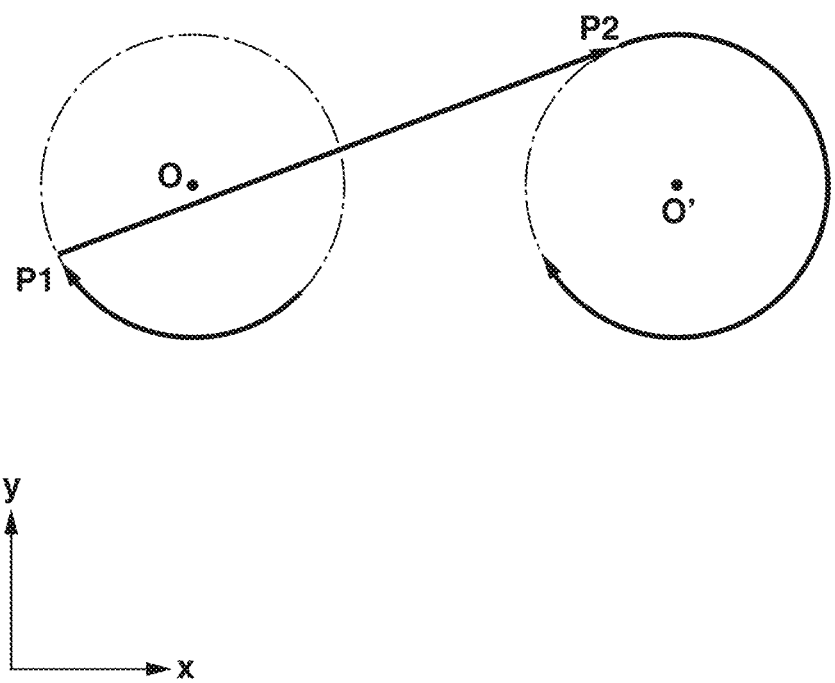
FIG. 4 illustrates another motion of the probe according to the first exemplary embodiment of the present invention.

According to the present exemplary embodiment, when a distance d1 between the points P1 and P2 exceeds a threshold value, the control unit 109 controls the moving unit 110 to move the probe PB along the line segment connecting the points P1 and P2, as illustrated in FIG. 4. This control method gives priority to the movement of the probe PB to the measurement position designated by the operator although the fluid level of an impedance matching material held in the probe PB may be disturbed. Thus, the probe PB is quickly moved to the point P2, making it possible to shorten the wait time from the time at which the operator designates a measurement position to the time at which measurement is performed at the measurement position.

In this example, since the operator designates the point C2' as a measurement position, the control unit 109 determines the point P2 so that a range including the point C2' can be measured. In determining the point P2 out of points on the circumference of the circle O', it is desirable that the point P2 is a point at which the straight line passing through the points P1 and P2 forms a tangent line of the circle O', and the direction from the point P1 toward the point P2 coincides with a vector indicating the moving direction of the probe PB at the tangent point. This enables the probe PB to be smoothly moved along the circular trajectory of the circle O' after being moved to the point P2.

Figure 5:
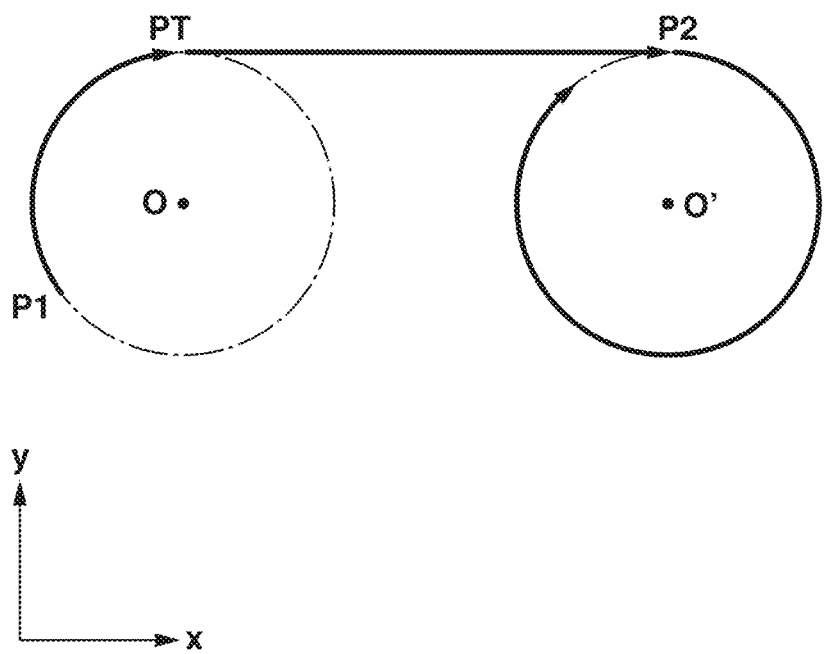
FIG. 5 illustrates yet another motion of the probe according to the first exemplary embodiment of the present invention.

On the other hand, in the case where the distance d1 between the points P1 and P2 is below the threshold value, the control unit 109 controls the moving unit 110 to move the probe PB along a gentler or more curved trajectory than in the case where the distance d1 exceeds the threshold value. An example is illustrated in FIG. 5. In the example illustrated in FIG. 5, instead of controlling the moving unit 110 to immediately move the probe PB from the point P1 along the line segment connecting the points P1 and P2, the control unit 109 controls the moving unit 110 to continue moving the probe PB along the circumference of the circle O. More specifically, the moving unit 110 moves the probe PB along a curve (circular arc) having a tangent line in the direction in which the probe PB passes through the point P1 as a first point. Then, after the probe PB is moved to a point PT, the probe PB is moved away from the circular trajectory of the circle O, and is moved along the straight line connecting the point PT and a point P2 on the circle O'. The straight line passing through the points PT and P2 is a common tangent line of the circles O and O'. Thus, when the probe PB is moved from the point P1 to the point PT along the circumference of the circle O, the probe PB can be tangentially moved away from the circular trajectory of the circle O and then is tangentially moved onto the circular trajectory of the circle O'. As a result, there is an advantage that the fluid level of the impedance matching material held in the probe PB is rarely disturbed. When the points P1 and P2 are close to each other, higher priority is given to the prevention of disturbance of the fluid level of the impedance matching material, i.e., the feasibility of continuous measurement than to the moving time. Therefore, it is desirable to move the probe PB along the trajectory as illustrated in FIG. 5. Particularly in the form of displaying an image in real time, for best results it is important that the continuity of measurement is maintained.

As described above, priority is given to the time period until the probe PB is moved to the measurement position when a distant measurement position is designated, and priority is given to the continuity of measurement when a close measurement position is designated, so that an acoustic wave acquisition apparatus that meets an operator's demand can be provided.

Examples will be described of a trajectory along which the probe PB is moved from the circle O to the circle O' other than the trajectories illustrated in FIGS. 4 and 5.

Figure 6:
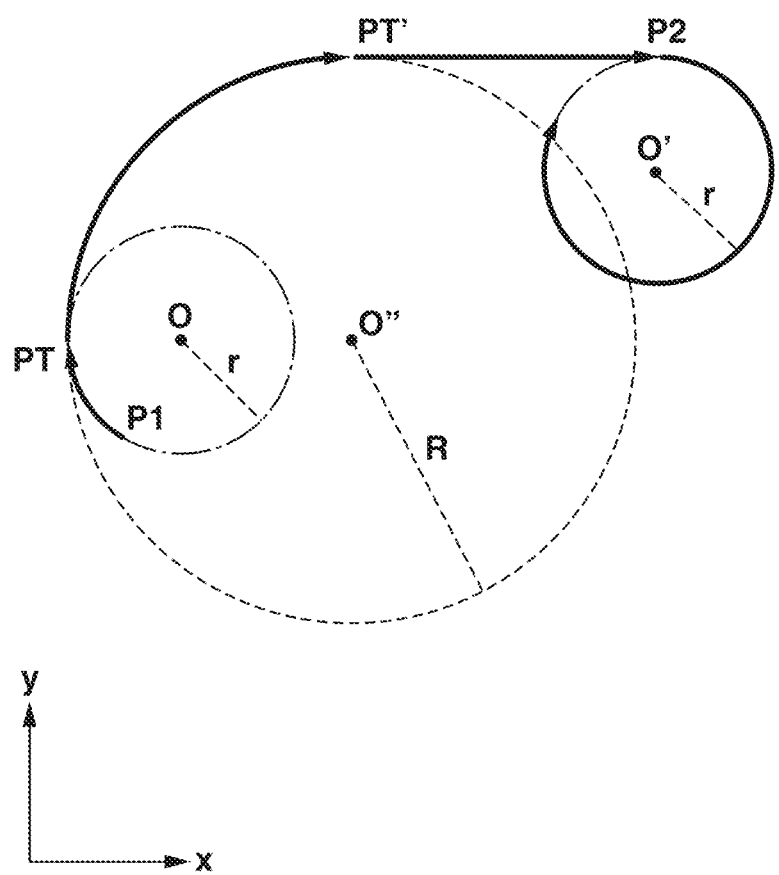
FIG. 6 illustrates yet another motion of the probe according to the first exemplary embodiment of the present invention.

FIG. 6 illustrates an example where the probe PB is moved from the point P1 to the point P2 along the circumference of a circle O" having a larger radius R than a radius r of the circle O. The circle O is inscribed in the circle O" at the point PT. The probe PB positioned at the point P1 is moved to the point PT along the circumference of the circle O, and then is moved from the point PT to a point PT' along the circumference of the circle O". In this case, the control unit 109 sets the position of the point P2 in such a way that the point P2 is a point at which the straight line passing through points PT' and P2 forms a common tangent line of the circles O" and O' and that the direction of a vector indicating the moving direction of the probe PB at the point P2 coincides with the direction from the point PT' toward the point P2. Accordingly, in the movement from the circle O to the circle O" and then in the movement from the circle O" to the circle O', the probe PB is tangentially moved away from one circular trajectory and then is tangentially moved onto another circular trajectory. This provides an effect of reducing the acceleration applied to the probe PB.

The relation between the radius r of the circle O and the radius R of the circle O" is not limited to "r<R". As illustrated in FIG. 7, the circular trajectory may satisfy a relation "r>R", i.e., the circle O" is inscribed in the circle O. In this case, since the probe PB can be moved to the straight line trajectory connecting the points PT' and P2 in a shorter time period than in the case illustrated in FIG. 6, this case is suitable when the distance connecting the points P1 and P2 exceeds a threshold value.

Figure 8:
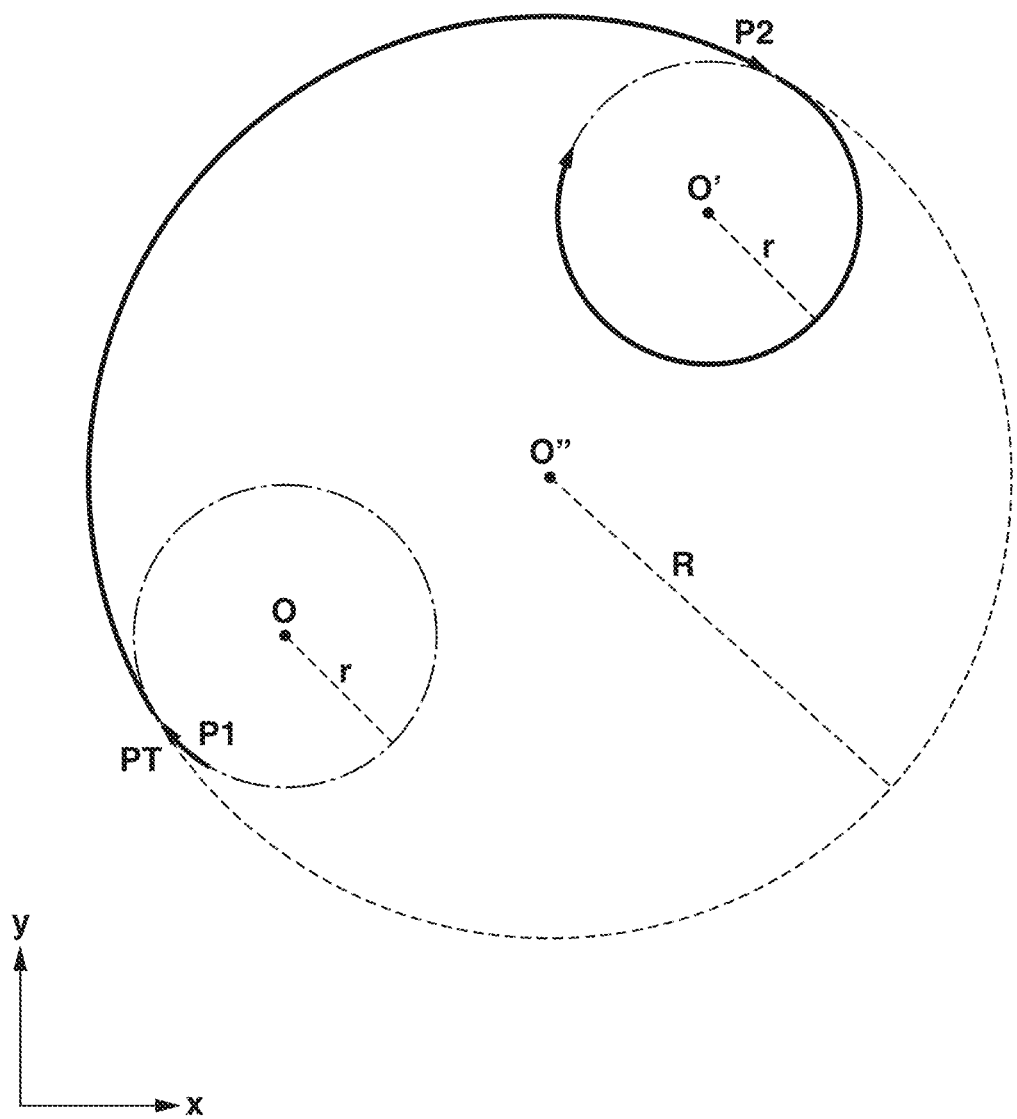
FIG. 8 illustrates yet another motion of the probe according to the first exemplary embodiment of the present invention.

FIG. 8 illustrates yet another method for moving the probe PB. Although each of the trajectories illustrated in FIGS. 4 to 7 includes a straight section, a trajectory not including a straight section may be set. In the example illustrated in FIG. 8, the control unit 109 moves the probe PB from the point P1 to the point P2 along the circumference of the circle O" in which the circles O and O' are inscribed.

The above-described problem can be solved for example by, of the above-described moving methods and any other ones, a method of moving the probe PB more linearly in the case where the distance between the points P1 and P2 exceeds a threshold value than in the case where the distance is below the threshold value. For example, when the distance between the points P1 and P2 exceeds the threshold value, the probe PB can be moved according to the pattern illustrated in FIG. 7. When the distance between the points P1 and P2 is below the threshold value, the probe PB can be moved according to the pattern illustrated in FIG. 6. A more linear trajectory means a smaller ratio of the length of the trajectory actually traced by the probe PB to the length of the line segment connecting the starting and ending points, i.e., the distance therebetween. The closer the ratio is to 1, the closer the trajectory of the probe PB is to the shortest distance. The larger the ratio is, the more curved and redundant the trajectory of the probe PB is.

Even when a measurement position is designated in the first image 201, in the case where the distance between the points P1 and P2 exceeds the threshold value, the moving unit 110 may move the probe PB more linearly than in the case where the distance is below the threshold value.

According to the present exemplary embodiment, even when a comparatively close position is designated as a measurement position in an apparatus on which the operator designates a measurement position, an effect that the orientation of a probe rarely becomes unstable can be obtained.

A second exemplary embodiment of the present invention will be described below. Further description of elements common to the first exemplary embodiment will be omitted.

The present exemplary embodiment differs from the first exemplary embodiment in that one of the first and the second images is displayed on a screen 900 and a unit for switching an image between the first and the second images is provided. In this case, a first image 901 captured by the first imaging unit 106 is displayed, and a frame 904 indicating the range currently being captured by the second imaging unit 107 is displayed in the first image 901. Photoacoustic measurement is performed on a range indicated by the frame 904. When the operator presses a button 905 as an image switching unit by using a cursor 903, the second image corresponding to the frame 904 is displayed. Likewise, when the operator presses the button 905 in a state where the second image is displayed on the display unit, the first image 901 is displayed.

Also according to the present exemplary embodiment, in the case where a position in the first image is designated as a measurement position, the moving unit 110 moves the probe PB to the measurement position more linearly than in the case where a position in the second image is designated as a measurement position. Even when a measurement position is designated in the first image, in the case where the distance between the points P1 and P2 exceeds the threshold value, the moving unit 110 may move the probe PB more linearly than in the case where the distance is below the threshold value.

Similar to the first exemplary embodiment, a photoacoustic image based on the acquired acoustic wave may be displayed on the screen 900 in addition to the first and second images.

Also according to the present exemplary embodiment, even when a comparatively close position is designated as a measurement position in an apparatus on which the operator designates a measurement position, an effect that the orientation of a probe rarely becomes unstable can be obtained.

A third exemplary embodiment of the present invention will be described below.

Although the first and the second exemplary embodiments have been described above centering on an acoustic wave acquisition apparatus having the first and second imaging units, the acoustic wave acquisition apparatus according to the present exemplary embodiment includes one imaging unit capable of changing the angle of view of an image to be captured.

As an example, the acoustic wave acquisition apparatus according to the present exemplary embodiment includes only the first imaging unit 106. The first imaging unit 106 has a zoom function so as to change the angle of view of the image to be captured.

A screen 1000 illustrated in FIG. 10 differs from the screen 900 illustrated in FIG. 9 according to the second exemplary embodiment in that a slider 1006 is provided as an angle of view change unit instead of the button 905.

According to the present exemplary embodiment, when the operator slides the slider 1006, the angle of view of the image 901 is changed. When the operator designates a measurement position in the case where the angle of view exceeds a predetermined threshold value, the control unit 109 moves the probe PB to the designated measurement position more linearly than in the case where the angle of view is below the predetermined threshold value.

Also according to the present exemplary embodiment, even when a comparatively close position is designated as a measurement position in an apparatus on which the operator designates a measurement position, an effect that the orientation of a probe rarely becomes unstable can be obtained.

Although the first to the third exemplary embodiments have been described above centering on examples of an image captured by an optical camera as a subject image to be used by the operator to designate a measurement position, the image is not limited to one captured by an optical camera and may be an image captured with the reflected ultrasound obtained by transmitting an ultrasonic wave to the subject or images captured by other modalities.

The present exemplary embodiment is also applicable to an acoustic wave acquisition apparatus for transmitting ultrasonic waves from a plurality of transducers 105 to the subject B and acquiring subject information based on the reflected wave.

The present exemplary embodiment has been described above centering on example cases where photoacoustic measurement is performed while the supporting unit 102 is moved along the circular trajectory, the trajectory is not limited to a circular trajectory and may be an elliptical trajectory and trajectories indicated by a rose curve represented by $r=a \cdot \sin(n\theta)$.

The operator can drag the frames 204 and 904 in designating a measurement position. In this case, the moving unit 110 may not move the probe PB while the operator is dragging the frame 204 and move the probe PB after a predetermined delay time has elapsed since the operator has finished dragging the frame 204. If the moving unit 110 moves the probe PB following the dragging of the frame 204, the fluid level of the acoustic matching material held in the supporting unit 102 may be unnecessarily disturbed. Therefore, it can be recognized that measurement position designation has not been completed while the operator is dragging the frame 204.

According to the present exemplary embodiment, even when a comparatively close position is designated as a measurement position in an apparatus on which the operator designates a measurement position, an effect that the orientation of a probe rarely becomes unstable can be obtained.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-224384, filed Nov. 17, 2016, which is hereby incorporated by reference herein in its entirety.

What is claimed is:

1. An acoustic wave acquisition apparatus comprising:
a probe configured to receive an acoustic wave propagated from a subject;
a moving unit configured to move the probe relative to the subject;
a target position designation unit configured to designate a target position to which the probe is to be moved; and
a movement control unit configured to control the moving unit to move the probe along a trajectory,
wherein the movement control unit determines the trajectory so that, in a case where a distance between the probe positioned at a first point and a second point corresponding to the target position is below a predetermined threshold value, a ratio of a length of the trajectory to a distance between the first point and the second point is larger than in a case where the distance between the probe and the second point exceeds the threshold value.

2. The acoustic wave acquisition apparatus according to claim 1, wherein the probe includes:
a supporting unit having a concave portion configured to hold an acoustic matching material; and
a plurality of acoustic wave detection elements disposed along the concave portion.

3. The acoustic wave acquisition apparatus according to claim 1, wherein the movement control unit moves the probe along a curve such that a line extending in a direction in which the probe passes through the first point is a tangent line of the curve.

4. The acoustic wave acquisition apparatus according to claim 3, wherein the movement control unit moves the probe along the curve, and moves the probe along a straight line from a position where the tangent line of the curve passes through the first point to the second point.

5. The acoustic wave acquisition apparatus according to claim 3, wherein the curve is a circular arc passing through the first point and the second point.

6. A method for controlling an acoustic wave acquisition apparatus including a probe configured to receive an acoustic wave propagated from a subject, and a moving unit configured to move the probe relative to the subject, the method comprising:
displaying an image of the subject;
receiving an input of a target position in the image; and
moving the probe according to the input of the target position,
wherein, in a case where a distance between the probe and a position corresponding to the target position is below a threshold value, a ratio of a length of a trajectory along which the probe is moved to the distance is larger than in a case where the distance exceeds the threshold value.

7. An acoustic wave acquisition apparatus comprising:
a probe configured to receive an acoustic wave propagated from a subject;
a moving unit configured to move the probe relative to the subject;
a movement control unit configured to control a movement of the probe by the moving unit;
a display control unit configured to cause a display unit to display a first image of the subject captured at a first angle of view and a second image of the subject captured at a second angle of view narrower than the first angle of view; and
a position designation unit configured to designate a position in the first image or the second image,
wherein, in a case where a position in the second image is designated by the position designation unit, the movement control unit moves the probe to a position corresponding to the designated position along a more curved trajectory than in a case where a position in the first image is designated.

8. The acoustic wave acquisition apparatus according to claim 7, wherein, in a case where a position in the first image is designated by the position designation unit, the movement control unit moves the probe to a position corresponding to the designated position along a trajectory including a straight section.

9. The acoustic wave acquisition apparatus according to claim 7, wherein the probe includes:
a supporting unit having a concave portion configured to hold a liquid; and
a plurality of acoustic wave detection elements disposed in the concave portion, and configured to receive the acoustic wave and convert the acoustic wave into an electrical signal.

10. The acoustic wave acquisition apparatus according to claim 7, further comprising an imaging unit configured to capture the first image and the second image.

11. The acoustic wave acquisition apparatus according to claim 10, wherein the imaging unit includes:
a first imaging unit configured to capture the first image; and
a second imaging unit configured to capture the second image.

12. The acoustic wave acquisition apparatus according to claim 11, wherein the first imaging unit and the second imaging unit capture the subject from different directions than each other.

13. The acoustic wave acquisition apparatus according to claim 10, wherein the imaging unit includes a zoom function of changing an angle of view of an image to be captured.

* * * * *